US 8,030,798 B2

(12) United States Patent
Seligman (10) Patent No.: US 8,030,798 B2
(45) Date of Patent: Oct. 4, 2011

(54) POWER SUPPLY FOR AN ELECTRONIC DEVICE

(75) Inventor: Peter Misha Seligman, Essendon (AU)

(73) Assignee: Cochlear Limited, MacQuarie University, NSW (AU)

( * ) Notice: Subject to any disclaimer, the term of this patent is extended or adjusted under 35 U.S.C. 154(b) by 0 days.

(21) Appl. No.: 12/649,164

(22) Filed: Dec. 29, 2009

(65) Prior Publication Data

US 2010/0219793 A1    Sep. 2, 2010

Related U.S. Application Data

(60) Division of application No. 11/645,729, filed on Dec. 27, 2006, now Pat. No. 7,638,898, which is a continuation of application No. 10/250,705, filed as application No. PCT/AU2002/000074 on Jan. 24, 2002, now Pat. No. 7,157,808.

(30) Foreign Application Priority Data

Jan. 24, 2001  (AU) .................................... PR2693

(51) Int. Cl.
*H02J 1/10* (2006.01)
*H02J 1/00* (2006.01)

(52) U.S. Cl. ................ 307/48; 307/64; 307/66; 307/71; 307/86

(58) Field of Classification Search .................... 307/44, 307/50, 71, 80, 85–86, 48, 64, 66
See application file for complete search history.

(56) References Cited

U.S. PATENT DOCUMENTS

| 3,930,192 A | 12/1975 | Dinkler |
| 4,081,738 A | 3/1978 | Roller |
| 4,175,249 A * | 11/1979 | Gruber ........................ 323/271 |
| 4,315,162 A | 2/1982 | Ferguson |
| 4,509,193 A | 4/1985 | Carlson |
| 4,532,930 A | 8/1985 | Crosby et al. |
| 4,563,621 A | 1/1986 | Moore |
| 4,614,905 A | 9/1986 | Petersson et al. |
| 4,955,729 A | 9/1990 | Marx |
| 5,003,244 A | 3/1991 | Davis, Jr. |

(Continued)

FOREIGN PATENT DOCUMENTS

WO         96/27932        9/1996

(Continued)

OTHER PUBLICATIONS

International Search Report of PCT/AU02/00074, dated Mar. 12, 2002.

(Continued)

*Primary Examiner* — Jared Fureman
*Assistant Examiner* — Adi Amrany
(74) *Attorney, Agent, or Firm* — Kilpatrick, Townsend & Stockton, LLP (57) ABSTRACT

A power supply for a medical device having one or more power consuming components. The power supply system comprises first and second battery cells electrically connected in series to supply a first level of power to the components, and at least one additional battery cell. The power supply also comprises a control system configured to electrically connect the at least one additional battery in parallel with one or both of the first or second batteries upon a detection of a power demand at the components that is greater than said first level.

36 Claims, 10 Drawing Sheets

U.S. PATENT DOCUMENTS

| | | | |
|---|---|---|---|
| 5,235,232 A * | 8/1993 | Conley et al. | 310/303 |
| 5,355,071 A | 10/1994 | Ishida et al. | |
| 5,387,857 A | 2/1995 | Honda et al. | |
| 5,488,282 A | 1/1996 | Hayden et al. | |
| 5,594,320 A | 1/1997 | Pacholok et al. | |
| 5,666,040 A | 9/1997 | Bourbeau | |
| 5,687,129 A | 11/1997 | Kim | |
| 5,696,833 A | 12/1997 | Matzen et al. | |
| 5,710,504 A | 1/1998 | Pascual et al. | |
| 5,742,150 A | 4/1998 | Khuwatsamrit | |
| 5,747,966 A | 5/1998 | Minamoto | |
| 5,767,660 A | 6/1998 | Schmidt | |
| 5,814,970 A | 9/1998 | Schmidt | |
| 5,821,729 A | 10/1998 | Schmidt et al. | |
| 5,876,425 A | 3/1999 | Gord et al. | |
| 5,880,575 A * | 3/1999 | Itou et al. | 320/122 |
| 5,956,241 A | 9/1999 | LoCascio | |
| 6,031,355 A | 2/2000 | Rich | |
| 6,064,178 A | 5/2000 | Miller | |
| 6,157,165 A | 12/2000 | Kinoshita et al. | |
| 6,222,344 B1 | 4/2001 | Peterson et al. | |
| 6,268,711 B1 * | 7/2001 | Bearfield | 320/117 |
| 6,281,662 B1 * | 8/2001 | Flohr | 320/141 |
| 6,358,281 B1 | 3/2002 | Berrang et al. | |
| 6,373,226 B1 * | 4/2002 | Itou et al. | 320/132 |
| 6,518,725 B2 | 2/2003 | Marten | |
| 6,624,535 B2 * | 9/2003 | Morrow | 307/71 |
| 6,636,751 B1 * | 10/2003 | McCartney | 455/572 |
| 6,815,931 B1 | 11/2004 | Wells et al. | |
| 6,841,971 B1 | 1/2005 | Spee et al. | |
| 6,879,855 B2 | 4/2005 | Schulman et al. | |
| 6,983,212 B2 | 1/2006 | Burns | |
| 7,157,808 B2 | 1/2007 | Seligman | |
| 7,288,919 B2 | 10/2007 | Morita | |
| 7,378,818 B2 | 5/2008 | Fowler et al. | |
| 7,409,068 B2 | 8/2008 | Ryan et al. | |
| 7,638,898 B2 | 12/2009 | Peter | |
| 2002/0109482 A1 | 8/2002 | Anzawa et al. | |
| 2002/0114982 A1 * | 8/2002 | Putt et al. | 429/3 |
| 2003/0139888 A1 | 7/2003 | Burns | |
| 2004/0113586 A1 | 6/2004 | Chen | |
| 2005/0140335 A1 | 6/2005 | Lee et al. | |
| 2006/0100674 A1 | 5/2006 | Molin | |
| 2007/0097719 A1 | 5/2007 | Parramon et al. | |
| 2009/0079265 A1 | 3/2009 | Seligman | |

FOREIGN PATENT DOCUMENTS

| | | |
|---|---|---|
| WO | 02/060029 | 8/2002 |

OTHER PUBLICATIONS

International Preliminary Examination Report of PCT/AU02/00074, dated Sep. 18, 2002.

International-Type Search Report, issued in connection with Australian Patent Application No. PR 2693, mailed Mar. 7, 2001.

* cited by examiner

FIG. 7
SIX PAIRS OF RAYOVAC CELLS

FIG. 9
LIMITING CURRENT vs. mA HOURS

FIG. 10

POWER SUPPLY FOR AN ELECTRONIC DEVICE

CROSS-REFERENCE TO RELATED APPLICATIONS

This application is a divisional application of U.S. patent application Ser. No. 11/645,729, filed Dec. 27, 2006, entitled "Power Supply for an Electronic Device," which is a continuation of U.S. patent application Ser. No. 10/250,705 filed on Jul. 7, 2003, entitled, "Power Supply for a Cochlear Implant," now issued as U.S. Pat. No. 7,157,808, which is a National Stage application of International Application PCT/AU2002/000074 filed on Jan. 24, 2002, entitled "Power Supply for a Cochlear Implant," and which claims priority to Australian Patent Application PR 2693, entitled "Power Supply for a Cochlear Implant," which was filed on Jan. 24, 2001. These above documents are hereby incorporated by reference herein.

BACKGROUND

1. Field of the Invention

The present invention relates generally to electronic devices, and more particularly, to a power supply for an electronic device.

2. Related Art

Hearing impairment, which may be due to many different causes, is generally of two types, conductive or sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often addressed with conventional hearing aids which amplify sound so that acoustic information can reach the cochlea.

In many people who are profoundly deaf, however, the reason for their deafness is sensorineural hearing loss. This type of hearing loss is due to the absence or destruction of the hair cells in the cochlea which transduce acoustic signals into nerve impulses. Those suffering from sensorineural hearing loss are thus unable to derive suitable benefit from conventional hearing aids due to the damage to or absence of these mechanisms for naturally generating nerve impulses from sound.

It is for this purpose that one type of auditory prosthesis, a cochlear implant (also commonly referred to as cochlear prosthesis, cochlear device, cochlear implant device, cochlear implant system and the like; generally and collectively sometimes referred to herein as a "cochlear implant") has been developed. As described in more detail below, a cochlear implant often includes an external component coupled to an internal component via a transcutaneous link. The internal component typically includes an array of stimulation electrodes implanted in the cochlea of the patient (referred to herein as a recipient). The electrode array is controlled by an electronic system encased in a hermetically sealed, biocompatible housing typically implanted in the mastoid. The electronic system, commonly referred to as a stimulator unit, essentially contains decoder and driver circuits for the stimulation electrodes. Acoustic sound reception and conversion of acoustic signals into electrical signals typically occurs in a speech processor. The speech processor may be worn by the recipient or may be implanted in the recipient. A microphone is typically located outside of the recipient's body, and may sometimes be positioned in a behind-the-ear housing worn on the auricle. Cochlear implants bypass the hair cells in the cochlea by directly delivering electrical stimulation to the auditory nerve fibers via the implanted electrode array. This enables the brain to perceive a hearing sensation resembling the natural hearing sensation normally delivered to the auditory nerve.

Like other electrically powered devices (simply electronic devices herein), components of a cochlear implant require a certain necessary amount of power so as to perform various operations. This necessary amount of power is typically supplied by a power supply comprising one or more battery cells. The power supply is integrated with, or electrically coupled to, the cochlear implant.

The amount of power necessary for proper operation may vary considerably from user to user, and from operation to operation. Furthermore, the amount of power required by components of the implant may depend on, for example, the stimulation rate employed by the implant to stimulate the cochlea, the speech processing strategy employed to convert a received sound to an electrical signal, etc. As would be appreciated, higher stimulation rates and more complicated speech processing strategies require larger amounts of power.

Similarly, the power requirements are also strongly influenced by recipient characteristics, such as the thickness of the skin separating the elements of the external and internal components that comprise the transcutaneous link. Larger skin flaps require larger amounts of power to transmit information and power there through.

As such, a power supply employed in a cochlear implant should be designed to supply various amounts of power so that the power supply does not need to be customized based on recipient characteristics, or on the device capabilities. However, with the introduction of new technologies, the size of cochlear implants, and particularly the size of the external components, is rapidly being reduced. These reduced sizes lead to restrictions in the type, size and dimension of the power supplies which may be utilized in cochlear implants.

SUMMARY

In one aspect of the present invention a power supply system for a medical device comprising one or more power consuming components is provided. The power supply system comprises: first and second battery cells electrically connected in series to supply a first level of power to the components; at least one additional battery cell; and a control system configured to electrically connect the at least one additional battery cell in parallel with one of the first or second battery cells upon a detection of a power demand at the components that is greater than said first level.

In another aspect of the present invention a power management system for a medical device comprising one or more power consuming components and first and second battery cells electrically connected in series to supply a first level of power to the components and at least an additional battery cell is provided. The management system comprises: a control system configured to electrically connect the at least one additional battery cell in parallel with one of the first or second battery cells upon a detection of a power demand at the components that is greater than said first level.

In a still other aspect of the present invention a method for supplying power to components of a medical device with a power supply comprising first, second and third battery cells is provided. The method comprises: electrically connecting the first and second battery cells in series to supply a first level of power; determining that the power demanded by one or more of the components exceeds the first power level; and electrically connecting the third battery cell in parallel with one of the first or second battery cells.

In another aspect of the present invention a medical device is provided. The medical device comprises: one or more power consuming components; first and second battery cells electrically connected in series to supply a first level of power to the components; at least one additional battery cell; a control system configured to electrically connect the at least one additional battery cell in parallel with one or both of the first or second battery cells upon a detection of a power demand at the components that is greater than said first level.

BRIEF DESCRIPTION OF THE DRAWINGS

Illustrative embodiments of the present invention are described herein with reference to the accompanying drawings, in which.

DETAILED DESCRIPTION

Aspects of the present invention are generally directed to a power supply for an electronic device. The power supply comprises a plurality of selectively electrically connectable battery cells configured to supply power to one or more components of the electronic device. Specifically, in certain embodiments the power supply comprises first and second battery cells electrically connected in series to supply a first level of power to the device components. The power supply further comprises at least one additional battery cell, and a control system to electrically connect the at least one additional battery cell in parallel with one or both of the first or second battery cells when a power demand exceeding the first level is detected.

A power supply in accordance with embodiments of the present invention may be used to supply power to various types of electronic devices. In one specific implementation described herein, embodiments of the present invention may be used to provide power to medical prostheses, such as a tissue-stimulating prosthesis. Embodiments of the present invention will be discussed herein with reference to one specific type of tissue-stimulating prosthesis, namely a cochlear implant.

Figure 1:
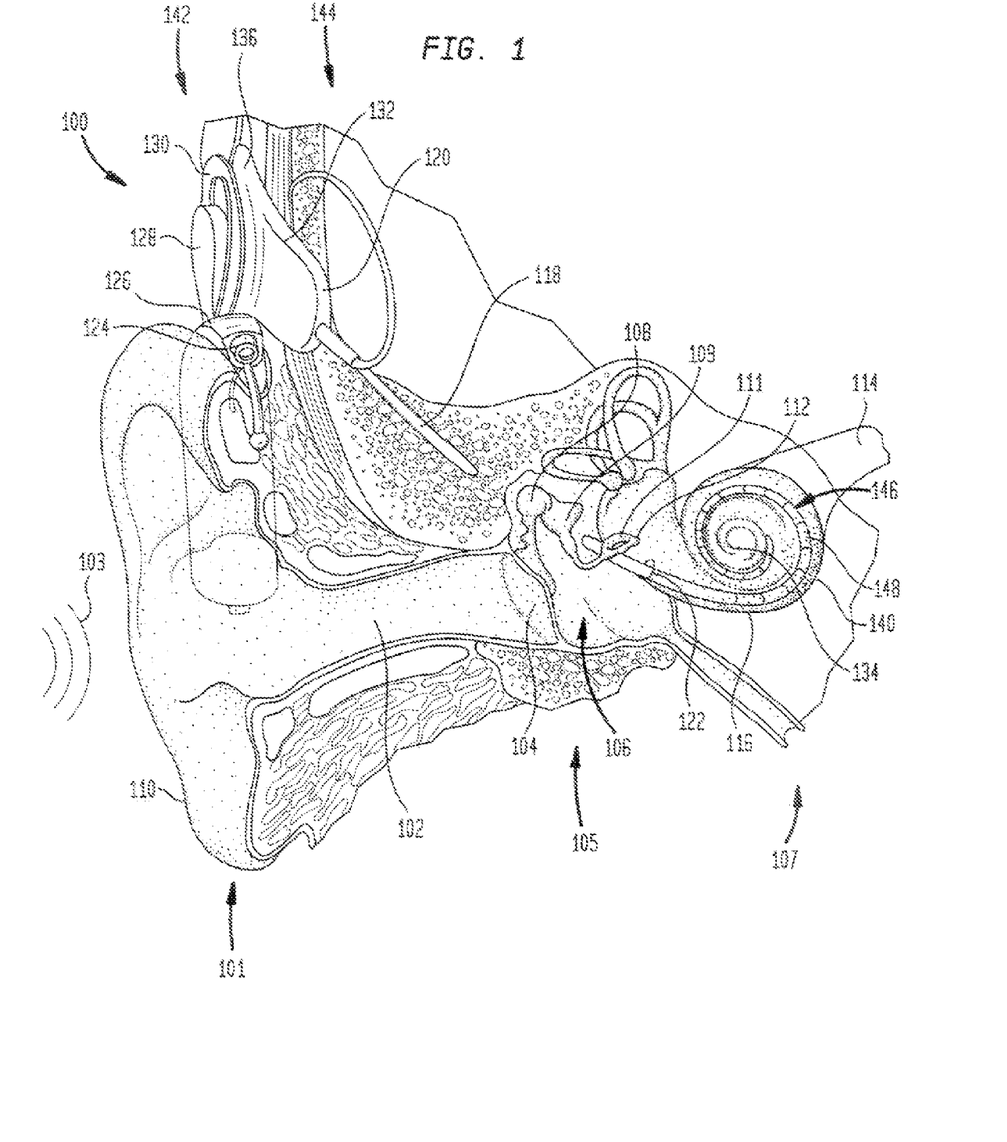
FIG. 1 is a perspective view of an exemplary medical prosthesis, namely a cochlear implant, in which embodiments of the present invention may be advantageously implemented.

FIG. 1 is perspective view of one embodiment of a cochlear implant 100 in which embodiments of the present invention may be advantageously implemented. The relevant components of outer ear 101, middle ear 105 and inner ear 107 are described next below, followed by a description of cochlear implant 100. Outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate. Such vibration sets up waves of fluid motion within cochlea 140. Such fluid motion, in turn, activates tiny hair cells (not shown) that line the inside of cochlea 140. Activation of the hair cells causes appropriate nerve impulses to be transferred through the spiral ganglion cells and auditory nerve 114 to the brain, where they are perceived as sound.

Cochlear implant 100 comprises external component 142 which is directly or indirectly attached to the body of the recipient, and an internal component 144 which is temporarily or permanently implanted in the recipient. External component 142 may comprise a microphone 124 for detecting sound, an external housing 126 having speech processing elements therein, and an external transmitter unit 128. As described in more detail below, a power supply (not shown) in accordance with embodiments of the present invention may also be included in external component 142.

As shown in FIG. 1, external transmitter unit 128 comprises an external coil 130 and, preferably, a magnet (not shown) secured directly or indirectly to external coil 130. The speech processing elements within housing 126 are configured to process the output of microphone 124 that is positioned, in the depicted embodiment, on auricle 110 of the recipient. The speech processing elements generate coded signals, referred to herein as a stimulation data signals, which are provided to external transmitter unit 128 via a cable (not shown). As discussed in more detail below, the power supply of external component 142 is configured to supply necessary power to other components of cochlear implant 100.

Internal component 144 comprises an internal receiver unit 132, a stimulator unit 120, and an elongate electrode carrier 118. Internal receiver unit 132 comprises an internal transcutaneous transfer coil 136, and preferably, a magnet (also not shown) fixed relative to the internal coil. Internal receiver unit 132 and stimulator unit 120 are hermetically sealed within a biocompatible housing. Internal coil 136 receives power and stimulation data from external coil 130, as noted above. Elongate electrode carrier 118 has a proximal end connected to stimulator unit 120 and extends from stimulator unit 120 to cochlea 140. Electrode carrier 118 is implanted into cochlea 104 via a cochleostomy 122.

Electrode carrier 118 comprises an electrode array 146 disposed at the distal end thereof. Electrode array 146 comprises a plurality of longitudinally-aligned electrodes 148. Stimulation signals generated by stimulator unit 120 are applied by electrodes 148 to cochlea 140, thereby stimulating auditory nerve 114.

In one embodiment, external coil 130 transmits electrical signals (i.e., power and stimulation data) to the internal coil via a radio frequency (RF) link. The internal coil is typically a wire antenna coil comprised of multiple turns of electrically insulated single-strand or multi-strand platinum or gold wire. The electrical insulation of the internal coil is provided by a flexible silicone molding (not shown). In use, implantable receiver unit 132 may be positioned in a recess of the temporal bone adjacent auricle 101 of the recipient.

Figure 2:
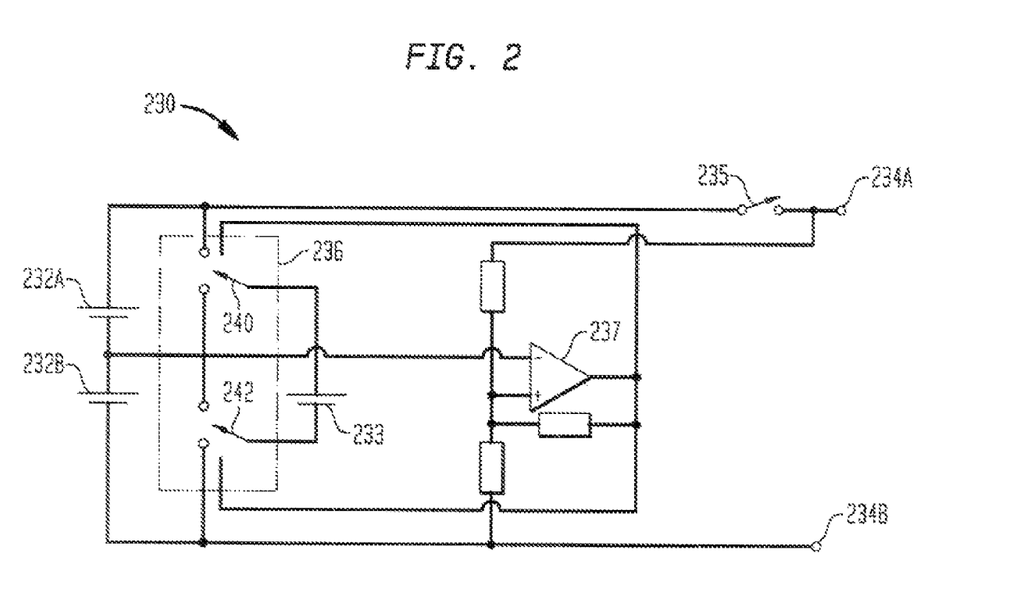
FIG. 2 is a schematic view of a power supply in accordance with embodiments of the present invention.

FIG. 2 is a schematic view illustrating the circuit layout of a power supply 230 in accordance with embodiments of the present invention. Power supply 230 may be configured for use with, for example, cochlear implant 100. As shown, power supply 230 comprises a first battery cell 232A and a second battery cell 232B electrically connected in series. In a first arrangement, electrically connected battery cells 232 are configured to supply power to one or more components of cochlear implant 100.

Power supply 230 further includes at least one additional battery cell 233, (sometimes referred to herein as "third battery cell"). As shown in FIG. 2, power supply 230 comprises a single additional battery cell 233. As discussed in more detail below, in other embodiments of the present invention, power supply 230 may comprise a plurality of additional battery cells 233.

As discussed below in more detail, third battery cell 233 is configured to be electrically connected in parallel with whichever of first or second battery cells 232 is determined to be exhibiting worse performance. Third battery cell 233 may be electrically connectable in parallel with either first or second battery cell 232 via a switch arrangement 236 comprising, in this embodiment, first and second switches 240, 242. In embodiments of the present invention, switch arrangement 236 comprises one or more analog changeover switches. Following connection of third battery cell 233 in parallel with one of first or second battery cells 232, the electrically connected first, second and third battery cells supply power to the implant components.

In certain embodiments of the present invention, the performance of battery cells 232 may be determined by comparing the voltages of battery cells 232 to one another. In these embodiments, the battery cell 232 having the lower voltage is determined to be exhibiting worse performance.

In other embodiments of the present invention, the performance of battery cells 232 may be determined by comparing the voltages of battery cells 232 to a predetermined threshold voltage. In these embodiments, if the voltage of one of battery cells 232 falls below the predetermined threshold or reference voltage, the one battery cell is determined to be exhibiting worse performance.

In embodiments of the present invention, power supply 230 comprises a control system to control the operation of switch arrangement 236. The control system may be further configured to evaluate the voltages of battery cells 232. As shown in FIG. 2, an exemplary control system in accordance with embodiments of the present invention comprises a low power comparator 237 and associated circuitry connected to switch arrangement 236. However, it would be appreciated that other implementations for a control system are within the scope of the present invention.

In the embodiments of FIG. 2, the voltage of each of first and second battery cells 232 is provided to comparator 237. Comparator 237 then compares the voltages of first and second battery cells 232 to one another, or to a predetermined threshold voltage. If the voltage of one of battery cells 232 is lower than the voltage of the other of battery cells 232, or is below the predetermined threshold voltage, comparator 237 causes switch arrangement 236 to connect third battery cell 233 in parallel with whichever of the first or second battery cells 232 has the lower voltage. In embodiments of the present invention, a small amount of hysteresis (eg. about 4 mV) is built into comparator 237 to avoid excessive switching of switch 236.

In other aspects of the present invention, third battery cell 233 may be connected in parallel with one or both of first or second battery cells 232 when power requirements of the implant components exceeds a power output by the first and second battery cells 232. In specific such embodiments, the third battery cell 233 may be connected in parallel with one or both of first or second battery cells 232 when power requirements of the implant components exceeds the maximum power available from first and second series-connected battery cells 232 alone.

In certain embodiments, when power requirements of the implant components exceed the power output by the first and second series-connected battery cells 232, comparator 237 determines which one of the first and second battery cells is exhibiting worse performance in one of the manners described above. Third battery cell 233 is then connected in parallel with whichever of first and second battery cells is exhibiting worse performance. The three batteries 232A, 232B and 233 collectively supply the larger amount of power to the implant components. Such embodiments ensure that power supply 230 is able to meet various power demands resulting from recipient characteristics or device requirements, such as large skin flaps, high stimulation rates or complicated speech processing strategies.

In certain embodiments of the present invention, because third battery cell 233 approximately halves the power demand of battery cell 232 with which the third battery is connected in parallel, the stored charge of the other of the first and second battery cells 232 will be reduced at a faster rate than the stored charges of the battery cells connected in parallel. Therefore, in such embodiments, to prevent an uneven depletion of batteries 232, power supply system 230 may be configured to alternate which third battery cell 233 is connected in parallel. In these embodiments, the control system actuates switching arrangement 236 so as to alternatively connect first and second battery cells 232 in parallel with third battery cell 233 at a regular frequency to ensure that the charge stored in first and second batteries 232 is depleted approximately equally. Power supply system 230 may be configured to alternate third battery 233 between first and second batteries 232 based on voltages measured by, for example, comparator 237.

It should be appreciated that further embodiments of the present invention include methods for supplying power to components of an electronic device, such as cochlear implant 100. In these embodiments, the method comprises the steps of electrically connecting first and second battery cells in series, and selectively electrically connecting a third battery cell in parallel with whichever battery of the first or second battery cells exhibits worse performance. As described above, in certain embodiments, a determination of which one of the first or second battery cells exhibits worse performance is made by comparing the voltages of the first and second batteries to one another. Also as described above, in other specific embodiments, a determination of which one of the first or second battery cells exhibits worse performance is made by comparing the voltages of the first and second battery cells to a predetermined threshold voltage.

In making the above determinations, the voltages of the battery cells may be measured by the power supply. In certain embodiments, the voltages of the first and second battery cells are measured with the third battery disconnected from each of the first and second battery cells.

Figure 3:
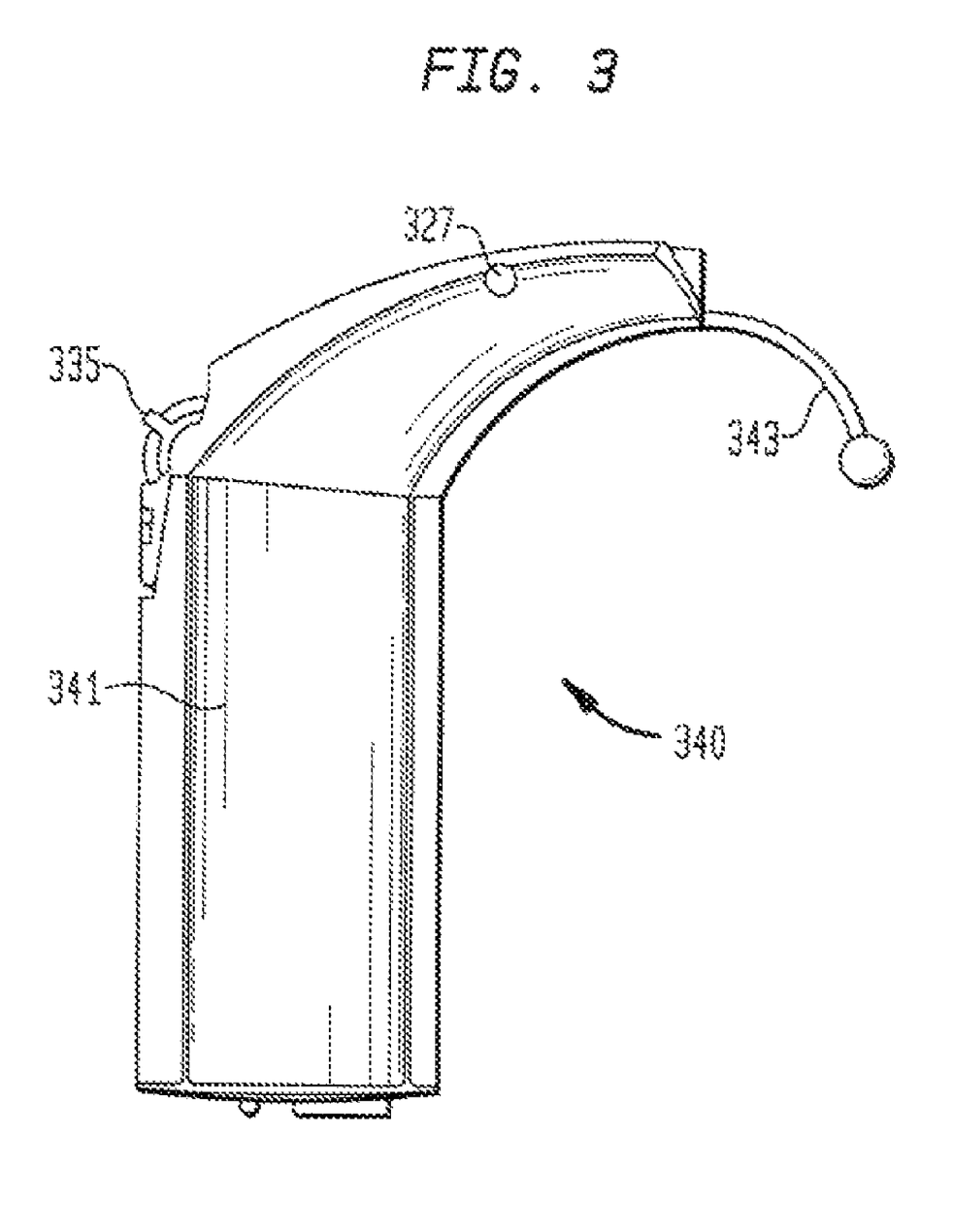
FIG. 3 is a side view of an external component of a cochlear implant in which embodiments of the present invention may be implemented.

FIG. 3 illustrates a specific embodiment of external component 142 of FIG. 1, commonly referred to as a Behind-The-Ear component (BTE) 340, in which power supply 230 of FIG. 2 may be implemented in accordance with certain aspects of the present invention. BTE 340 is an external unit configured to be positioned behind-the-ear of a recipient of cochlear implant 100. BTE 340 may have therein or thereon various components of a cochlear implant 100, such as a microphone 327 and speech processing elements (not shown).

Figure 4:
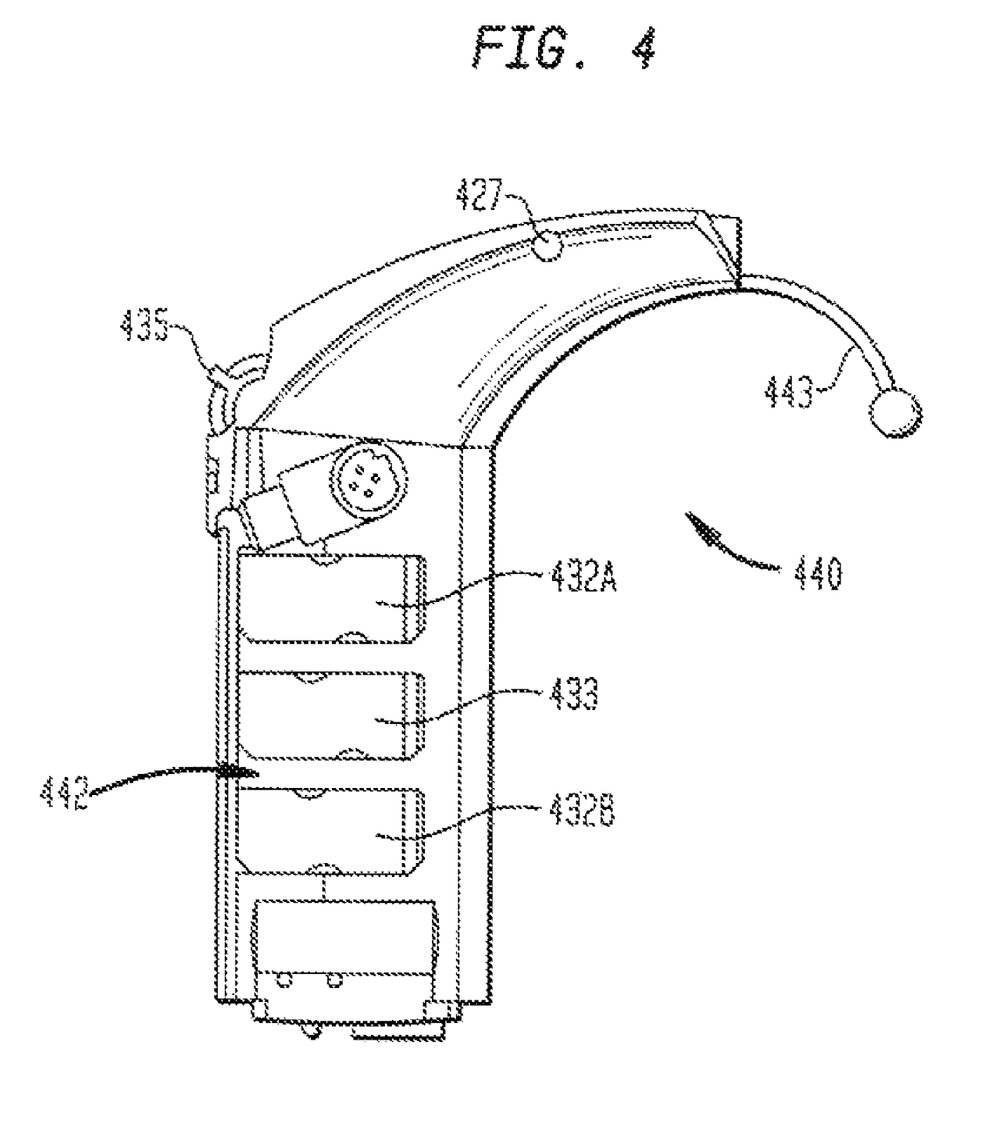
FIG. 4 is a side view of the external component of FIG. 3 having a portion of the exterior housing removed.

In the embodiment of FIG. 3, BTE 340 comprises a removable cover 341 enclosing a battery compartment (not shown). An exemplary battery compartment is illustrated in FIG. 4 as battery compartment 442. BTE 340 further comprises ear hook 343 for retaining the BTE on an auricle of the recipient, and an On/Off switch 335.

FIG. 4 illustrates an embodiment of BTE 340, referred to herein as BTE 440. In the illustrated embodiment, cover 341 (FIG. 3) has been removed to expose battery compartment 442. In the illustrated embodiment, battery compartment 442 has positioned therein a power supply comprising battery cells 432A, 432B and 433, and a switch (not shown). In a first configuration, battery cells 432A and 432B are electrically connected in series to supply power to other components of the cochlear implant, such as microphone 427, speech processing elements, the implanted electrode array, or any other electrical or electronic component of the cochlear implant whether it be external or internal of the body of the recipient. In a second configuration, battery cell 433 is configured to be electrically connected in parallel with one of first or second battery cells 432 in the same manner as described above with reference to FIG. 2.

Although FIG. 4 illustrates battery cells 432A, 432B and 433 mounted within a housing that also encloses other components of cochlear implant 100, it should be appreciated that in other embodiments, battery cells 432A, 432B and 433 may be mounted within a separate housing. In such exemplary embodiments, an electrical connection would be provided between the battery cells/power supply system and the other components of cochlear implant 100.

It should be appreciated that any suitable battery cell may be utilized in conjunction with embodiments of the present invention. However, in certain embodiments battery cells 432A, 432B and 433 may each comprise a zinc-air cell. The use of zinc air cells may provide several practical advantages over other types of battery cells, including a comparatively high energy density that can supply a device's requirements for a long period of time relative to their size and weight. Also, zinc air cells have a relatively constant power output throughout most of their life, thereby reducing the risk of dangerous rapid discharge, such as shorting. It should also be appreciated that in certain embodiments, when mounted in a medical prosthesis, each of battery cells 432A, 432B and 433 may be surrounded by an electrically insulating material such that the battery cells are electrically insulated from each other and from the housing in which they are mounted.

In certain embodiments of the present invention, battery cells 432A, 432B and 433 are preferably all of the same design. However, in other embodiments of the present invention, one or more of battery cells 432A, 432B or 433 may be of a different design.

In certain embodiments of the present invention one or more of batteries battery cells 432A, 432B or 433 may comprise a rechargeable battery cell. In such embodiments, a power supply in accordance with embodiments of the present invention may also include one or elements to recharge the rechargeable battery cells.

Figure 5:
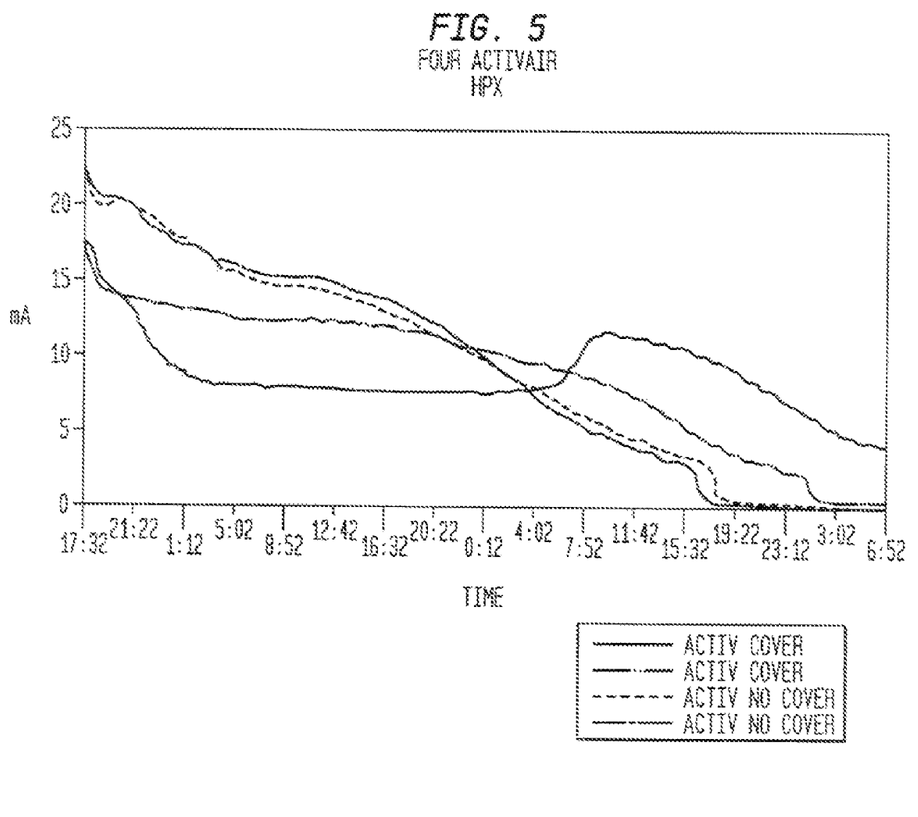
FIG. 5 is a graph illustrating typical limiting currents of four activair HPX battery cells.
Figure 6:
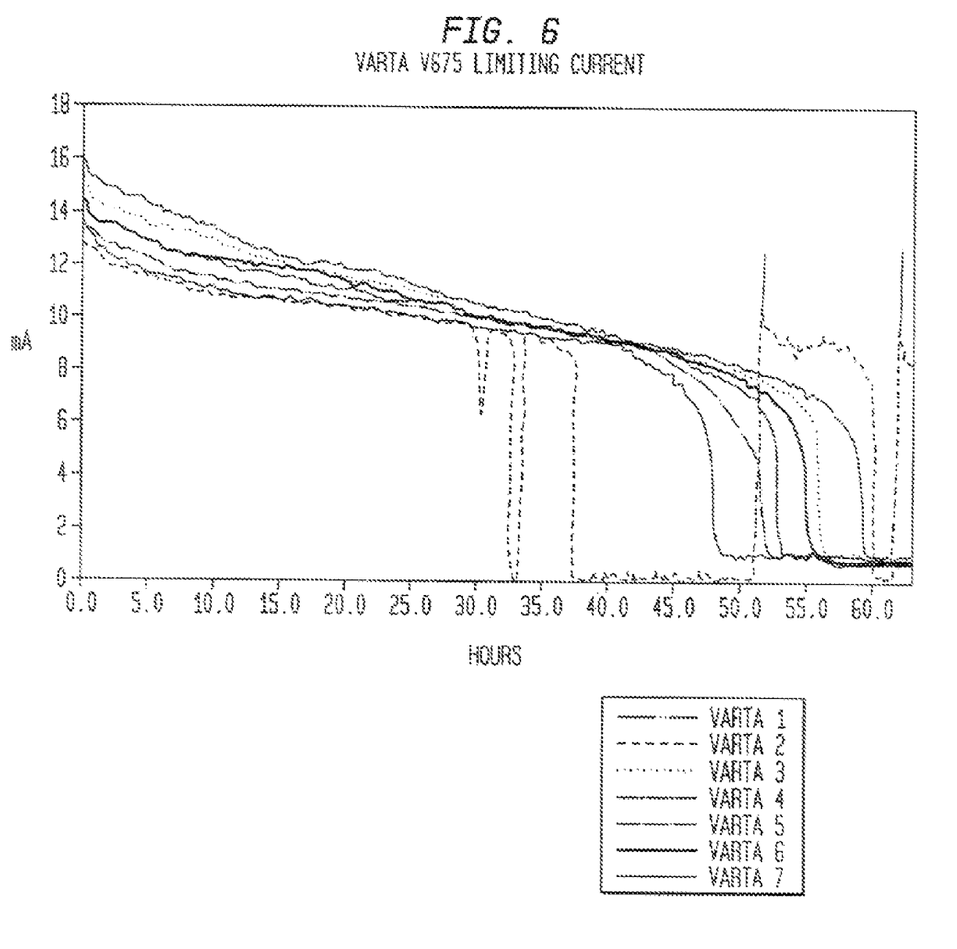
FIG. 6 is a graph illustrating limiting currents of seven VARTA® battery cells.
Figure 7:
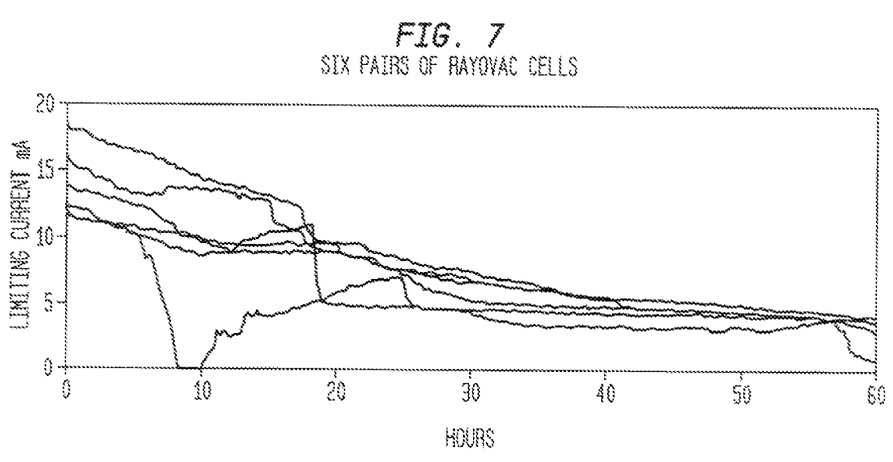
FIG. 7 is a graph illustrating limiting currents of six pairs of Rayovac® battery cells.

FIG. 5 is a graph illustrating typical limiting currents in mA vs. time for four 675 size zinc-air Activair BPX battery cells. FIG. 6 is a graph illustrating typical limiting currents for seven 675 size zinc-air Varta® V675 battery cells, again presented as limiting current in mA vs. time, while FIG. 7 is a graph illustrating the performance of six pairs of Rayovac® 675 size zinc-air cells, presented as limiting current in mA vs. time. As can be seen from FIGS. 5-7, the reliability of these cells is relatively poor, with the performance from one cell to the next being relatively inconsistent.

Figure 8:
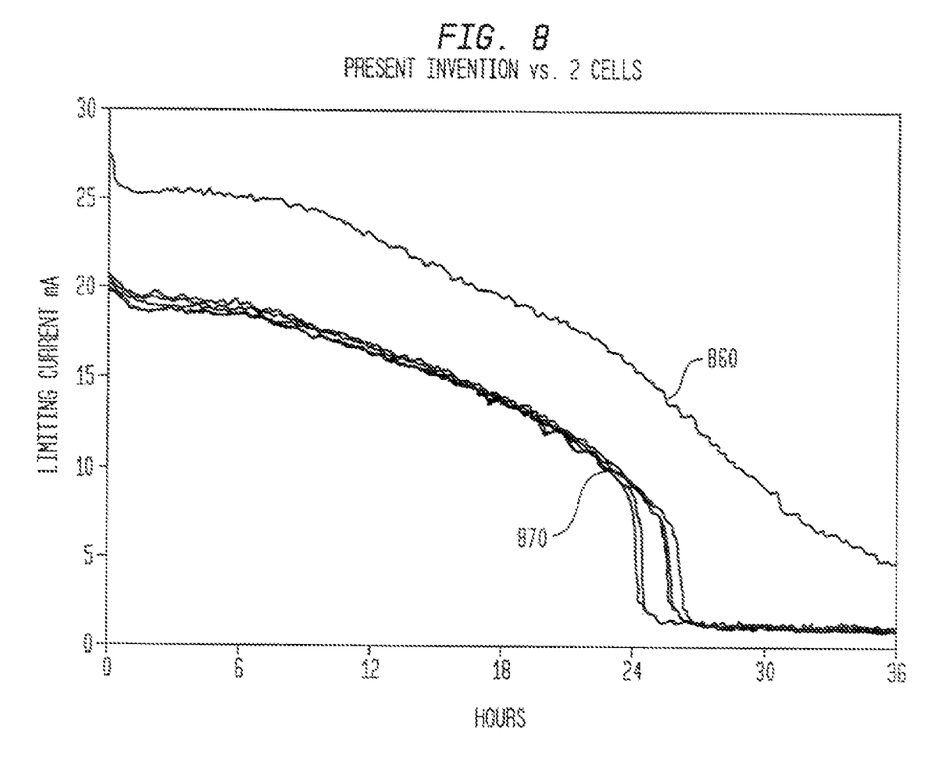
FIG. 8 is a graph illustrating the limiting current over time exhibited by a power supply in accordance with embodiments of the present invention in which three battery cells are selectively electrically connectable in series, and the limiting current over time exhibited by a two cell arrangement.
Figure 9:
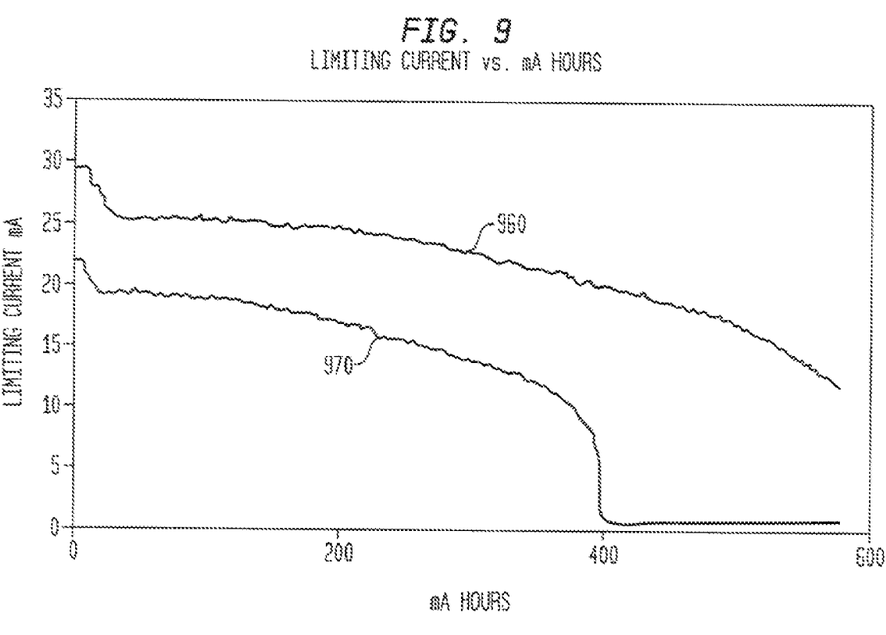
FIG. 9 is a graph illustrating the limiting current vs. mA hours in accordance with the arrangements illustrated in FIG. 8.
Figure 10:
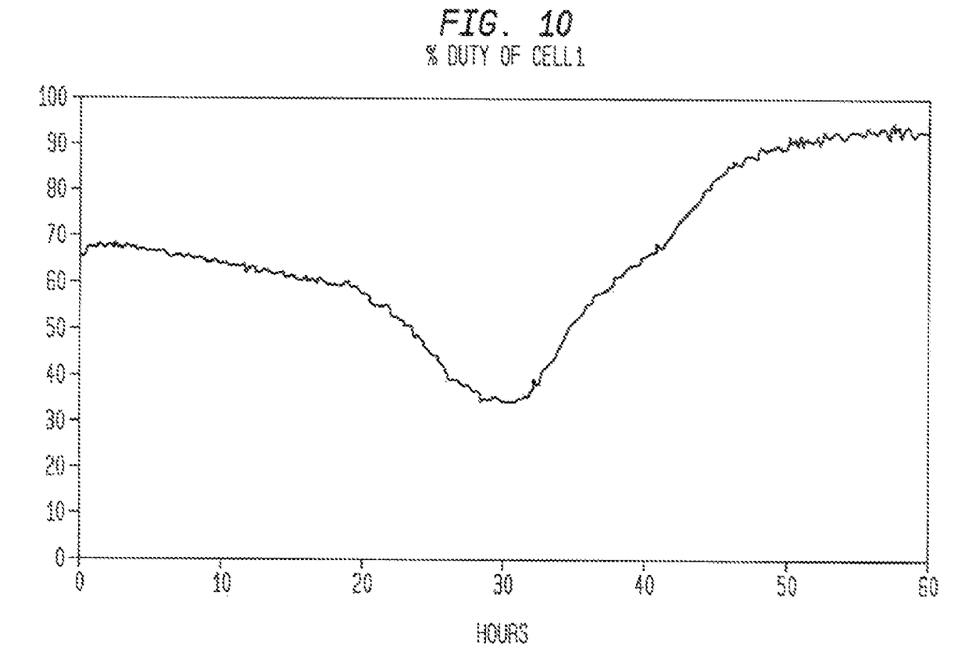
FIG. 10 is a graph illustrating the duty cycle of a battery cell utilized in embodiments of the present invention.

FIG. 8 is a graph illustrating the limiting current over time exhibited by a power supply in accordance with embodiments of the present invention. Line 860 represent the limiting current vs. time for a power supply in accordance with embodiments of the present invention when loaded by a constant 2.2 Volt load. More specifically, line 860 represents the limiting current for a configuration in which two battery cells are electrically connected in series, and in which an additional battery cell is configured to be connected in parallel to one or both of the other two battery cells. Lines 870 each represent the limiting current vs. time for various two cell power supply arrangements when loaded by a constant 2.2 Volt load. As can be seen in FIG. 8, the arrangement of the present invention significantly improves the limiting current of the power supply system such that a load current can be supplied for a longer time than could be supplied by two cell power supply arrangements. This is better shown in FIG. 9, which illustrates the limiting current vs. mA hours for embodiments of the present invention and for the two cell prior art arrangement. As can be seen, for an exemplary load current of 15 mA, the available power output capacity has increased from 268 mA hours for a prior art arrangement to approximately 536 mA hours for embodiments of the present invention.

While the illustrated and described embodiments comprise two battery cells placed in series and a third battery cell configured to be electrically connectable in parallel with either of the two series-connected battery cells, it is envisaged that additional battery cells may also be used. For example, embodiments of the present invention may employ more than two battery cells in series and more than one battery cell electrically connectable in parallel with one or more of the series-connected battery cells. Such embodiments should be considered within the scope of the present invention.

Similarly, the present invention has been discussed in reference to single battery cells. However, it should be appreciated that, as used herein, each battery cell may also refer to a plurality of battery cells.

For ease of description, the present invention has been described herein with reference to one electronic device, namely a cochlear implant. However, it should be appreciated that the above described power supply may be used with other electronic devices.

Furthermore, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

The invention claimed is:

1. A power supply system for a medical device comprising one or more power consuming components having a varying power demand, the system comprising:
   first and second battery cells electrically connected in series to supply power to the components;
   at least one additional battery cell; and
   a control system configured to electrically connect the at least one additional battery cell in parallel with one of the first and second battery cells in response to a detection that the power demand of the components has increased.

2. The system of claim 1, further comprising:
   a switch arrangement operable by the control system to electrically connect the at least one additional battery cell in parallel with one of the first and second battery cells.

3. The system of claim 2, wherein said switch arrangement comprises one or more analog changeover switches.

4. The system of claim 1, wherein the control system is configured to connect the at least one additional battery cell in parallel with whichever one of the first and second battery cells has a voltage below a threshold voltage.

5. The system of claim 4, wherein the control system comprises:
   a low power comparator configured to compare each the voltages of the first and second battery cells to a reference voltage to determine whether one of the first and second battery cells has a voltage below the threshold voltage.

6. The system of claim 1, wherein the control system is configured to connect the at least one additional battery cell in parallel with whichever one of the first and second battery cells has a lower voltage.

7. The system of claim 4, wherein the control system comprises:
   a low power comparator configured to compare the voltages of the first and second battery cells to one another to determine which of the first and second battery cells has a lower voltage.

8. The system of claim 1, wherein the control system is configured to alternate which of the first and second battery cells is connected in parallel with the at least one additional battery cell.

9. The system of claim 1, wherein at least one of the first and second battery cells comprises a rechargeable battery cell, and wherein the system further comprises:
   a charging circuit configured to recharge the at least one rechargeable battery cell when the voltage of the rechargeable cell is below a predetermined voltage level.

10. The system of claim 1, wherein one or more of said battery cells comprise a zinc air cell.

11. A power management system for a medical device comprising one or more power consuming components having a varying power demand, first and second battery cells electrically connected in series to supply power to the components, and at least an additional battery cell, the management system comprising:
   a control system configured to electrically connect the at least one additional battery cell in parallel with one of the first and second battery cells in response to a detection that the power demand of the components has increased.

12. The system of claim 11, further comprising:
   a switch arrangement operable by the control system to electrically connect the at least one additional battery cell in parallel with one of the first and second battery cells.

13. The system of claim 12, wherein said switch arrangement comprises one or more analog changeover switch.

14. The system of claim 11, wherein the control system is configured to connect the at least one additional battery cell in parallel with whichever one of the first and second battery cells has a voltage below a threshold voltage.

15. The system of claim 14, wherein the control system comprises:
   a low power comparator configured to compare each the voltages of the first and second battery cells to a reference voltage to determine whether one of the first and second battery cells has a voltage below the threshold voltage.

16. The system of claim 11, wherein the control system is configured to connect the at least one additional battery cell in parallel with whichever one of the first and second battery cells has a lower voltage.

17. The system of claim 16, wherein the control system comprises:
   a low power comparator configured to compare the voltages of the first and second battery cells to one another to determine which of the first and second battery cells has a lower voltage.

18. The system of claim 11, wherein the control system is configured to alternate which of the first and second battery cells is connected in parallel with the at least one additional battery cell.

19. The system of claim 11, wherein at least one of the first and second battery cells comprises a rechargeable battery cell, and wherein the system further comprises:
   a charging circuit configured to recharge the at least one rechargeable battery cell when the voltage of the rechargeable cell is below a predetermined voltage level.

20. The system of claim 11, wherein one or more of said battery cells comprise a zinc air cell.

21. A method for supplying power to components of a medical device with a power supply comprising first, second and third battery cells, the components having a varying power demand, the method comprising:
   electrically connecting the first and second battery cells in series to supply power to the components;
   determining that the power demanded by one or more of the components has increased; and
   electrically connecting the third battery cell in parallel with one of the first or second battery cells in response to the determination.

22. The method of claim 21, wherein the method further comprises:
   determining which of the first and second cells has a lower voltage; and
   electrically connecting the third battery cell in parallel with whichever of the first and second battery cells has the lower voltage.

23. The method of claim 22, wherein determining which of the first and second battery cells has a lower voltage comprises:
   comparing the voltages of the first and second battery cells to one another.

24. The method of claim 22, wherein determining which of the first and second battery cells has a lower voltage comprises:
   comparing the voltages of each of the first and second battery cells to a reference voltage.

25. The method of claim 21, wherein at least one of the battery cells comprises a rechargeable battery, and wherein the method further comprises:
recharging the at least one rechargeable battery cell.

26. The method of claim 21, wherein method further comprises:
alternating which of the first and second battery cells is connected in parallel with the at least one additional battery cell.

27. A medical device comprising:
one or more power consuming components having a variable power demand;
first and second battery cells electrically connected in series to supply power to the components;
at least one additional battery cell;
a control system configured to electrically connect the at least one additional battery cell in parallel with at least one of the first and second battery cells in response to a detection that the power demand of the components has increased.

28. The device of claim 27, further comprising:
a switch arrangement operable by the control system to electrically connect the at least one additional battery cell in parallel with one of the first and second battery cells.

29. The device of claim 28, wherein said switch arrangement comprises one or more analog changeover switches.

30. The device of claim 27, wherein the control system is configured to connect the at least one additional battery cell in parallel with whichever one of the first and second battery cells has a voltage below a threshold voltage.

31. The device of claim 30, wherein the control system comprises:
a low power comparator configured to compare each the voltages of the first and second battery cells to a reference voltage to determine whether one of the first and second battery cells has a voltage below the threshold voltage.

32. The device of claim 27, wherein the control system is configured to connect the at least one additional battery cell in parallel with whichever one of the first and second battery cells has a lower voltage.

33. The device of claim 32, wherein the control system comprises:
a low power comparator configured to compare the voltages of the first and second battery cells to one another to determine which of the first and second battery cells has a lower voltage.

34. The device of claim 27, wherein the control system is configured to alternate which of the first and second battery cells is connected in parallel with the at least one additional battery cell.

35. The device of claim 27, wherein at least one of the first and second battery cells comprises a rechargeable battery cell, and wherein the system further comprises:
a charging circuit configured to recharge the at least one rechargeable battery cell when the voltage of the rechargeable cell is below a predetermined voltage level.

36. The device of claim 27, wherein one or more of said battery cells comprise a zinc air cell.

* * * * *